United States Patent [19]
Roby et al.

[11] Patent Number: 5,716,376
[45] Date of Patent: Feb. 10, 1998

[54] ABSORBABLE MIXTURE AND COATINGS FOR SURGICAL ARTICLES FABRICATED THEREFROM

[75] Inventors: Mark S. Roby, Killingworth; Ying Jiang, North Haven; John S. Bobo, Guilford; Jon T. Reinprecht, Waterbury, all of Conn.

[73] Assignee: United States Surgical Corporation, Norwalk, Conn.

[21] Appl. No.: 671,902

[22] Filed: Jun. 28, 1996

[51] Int. Cl.⁶ ............................................. A61B 17/04
[52] U.S. Cl. ................................. 606/228; 606/230
[58] Field of Search ............................ 606/228, 230, 606/231; 428/378, 364, 394

[56] References Cited

U.S. PATENT DOCUMENTS

| | | | |
|---|---|---|---|
| 4,027,676 | 6/1977 | Mattei | 128/335.5 |
| 4,185,637 | 1/1980 | Mattei | 128/335.5 |
| 4,190,720 | 2/1980 | Shalaby | 528/354 |
| 4,201,216 | 5/1980 | Mattei | 128/335.5 |
| 4,532,929 | 8/1985 | Mattei et al. | 128/335.5 |
| 4,582,052 | 4/1986 | Dunn et al. | 128/130 |
| 4,605,730 | 8/1986 | Shalaby et al. | 528/357 |
| 4,624,256 | 11/1986 | Messier et al. | 128/335.5 |
| 4,700,704 | 10/1987 | Jamiolkowski et al. | 128/335.5 |
| 4,705,820 | 11/1987 | Wang et al. | 524/381 |
| 4,711,241 | 12/1987 | Lehmann | 128/335.5 |
| 4,788,979 | 12/1988 | Jarrett et al. | 128/335.5 |
| 4,791,929 | 12/1988 | Jarrett et al. | 128/335.5 |
| 4,994,074 | 2/1991 | Bezwada et al. | 606/230 |
| 5,032,638 | 7/1991 | Wang et al. | 524/400 |
| 5,047,048 | 9/1991 | Bezwada et al. | 606/231 |
| 5,100,433 | 3/1992 | Bezwada et al. | 606/230 |
| 5,133,739 | 7/1992 | Bezwada et al. | 606/230 |
| 5,352,515 | 10/1994 | Jarrett et al. | 428/357 |
| 5,380,780 | 1/1995 | Olson | 524/311 |
| 5,522,842 | 6/1996 | Shalaby | 606/230 |
| 5,609,609 | 3/1997 | Ohshima et al. | 606/231 |

OTHER PUBLICATIONS

Horton C.E., Adamson, J.E., Mladick R.A., et al, "Vicryl Synthetic Absorbable Sutures", pp. 729–731, Am Surg. Dec. 1974.

Saunder's R.A. et al.: "Coated Vicryl Suture in Extraocular Muscle Surgery". Ophthalmic Surg. 10:13-8, Jul. 1979.

Kobayashi H. et al. "Coated Polyglactin 910—a New Synthetic Absorbable Suture". Jpn J. Surg 11(6):467-75, Nov. 1981.

*Primary Examiner*—Michael Buiz
*Assistant Examiner*—Tina T. D. Pham

[57] ABSTRACT

Absorbable mixtures are fabricated from a predominant component of fatty acid ester mixed with a copolymer comprising a predominant amount of epsilon-caprolactone and a minor amount of at least one other copolymerizable monomer of other bioabsorbable monomers. These mixtures are useful in forming coating for surgical articles, including multifilament sutures.

17 Claims, 1 Drawing Sheet

ABSORBABLE MIXTURE AND COATINGS FOR SURGICAL ARTICLES FABRICATED THEREFROM

TECHNICAL FIELD

Absorbable materials fabricated from mixtures of caprolactone containing copolymers and esters of fatty acids, and more particularly coatings for surgical articles made totally or in part therefrom, including coatings for multifilament sutures, are provided.

BACKGROUND OF THE INVENTION

Synthetic absorbable multifilament sutures such as Dexon, Vicryl, and Polysorb commercially available from Davis & Geck (Danbury, Conn.), Ethicon, Inc. (Somerville, N.J.), and United States Surgical Corporation (Norwalk, Conn.), respectively, are well known in the industry.

Suture coatings for synthetic absorbable sutures containing caprolactone are well known, see for example U.S. Pat. Nos. 4,624,256; 4,190,720; 4,582,052; 4,605,730; 4,700,704; 4,705,820; 4,788,979; 4,791,929; 4,994,074; 5,047,048; 5,100,433; 5,133,739; 5,352,515. Suture coatings containing esters of fatty acids are also known see for example U.S. Pat. Nos. 5,032,638, 4,711,241, 4,705,820, and 4,027,676.

In the early 1970's Ethicon introduced uncoated Vicryl; see for example Horton C. E., Adamson J. E., Mladick R. A., et al: "Vicryl Synthetic Absorbable Sutures"; Am Surg, Dec. 1974,pp 72930–31. However, this uncoated braided multifilament caused tissue trauma (tissue drag) and handling problems. As a result, in the late 1970's a Vicryl suture coated with a glycolide/lactide copolymer blended with calcium stearate was introduced; see for example Saunder's R. A. et al: "Coated Vicryl Suture in Extraocular Muscle Surgery". Ophthalmic Surg 10:13–8. July 1979 and Kobayashi H et al. "Coated Polyglactin 910—a New Synthetic Absorbable Suture". Jpn J Surg 11 (6):467–75, November 1981. U.S. Pat. No. 4,201,216 discloses a glycolide/lactide copolymer blended with calcium stearate as a suture coating.

Although calcium stearate was used as a component in the Vicryl suture coating; the manufacture and application of such a suture coating would require an impractical and uneconomical dip coating process became calcium stearate (a hydrophobic metal salt of a fatty acid) generally is insoluble. Therefore, a suture coating fabricated from materials that would dissolve in solution and thus obviate the necessity of using dip coating processes would provide great manufacturing advantages.

Another important feature of a suture coating is its ability to enhance the suture's handling characteristics, such as surgeon's throw, lubricity, knot run down and/or knot security. Although commercially available surgical sutures such as Polysorb have excellent handling characteristics; it would be advantageous to provide a coated suture exhibiting even better surgeon's throw, lubricity, knot run down, and/or knot security properties.

SUMMARY OF THE INVENTION

It has now been found that such a coating for absorbable surgical articles may be formed from the mixture of a copolymer containing caprolactone with an ester of a fatty acid.

Preferably, mixtures useful in forming the aforementioned coatings include an ester of a fatty acid as a predominant component. A "predominant component" is a component which is present in an amount greater than about 50 weight percent. A "minor component" is a component which is present in an amount up to about 50 weight percent. The minor component comprises copolymers containing caprolactone.

Particularly useful caprolactone containing copolymers are "star" copolymers obtained by polymerizing a major amount of epsilon-caprolactone and a minor amount of another bioabsorbable monomer polymerizable therewith in the presence of a polyhydric alcohol initiator.

Particularly useful fatty acid esters include calcium stearolyl lactylate. Since such fatty acid esters are soluble, coatings fabricated from mixtures of such fatty acid esters and caprolactone containing polymers need not be applied to surgical articles by the undesirable dip coating process.

In a particularly useful embodiment the mixture may be applied to braided multifilament sutures. Preferably mixtures useful in this embodiment comprise at least about 52 percent fatty acid ester, the remainder being caprolactone containing copolymer. Applied to a suture, the coating composition results in advantageous improvement in one or more properties of the suture, e.g., knot security, surgeon's throw, lubricity, knot run down, and/or knot repositioning.

DESCRIPTION OF THE PREFERRED EMBODIMENTS

Figure 1:
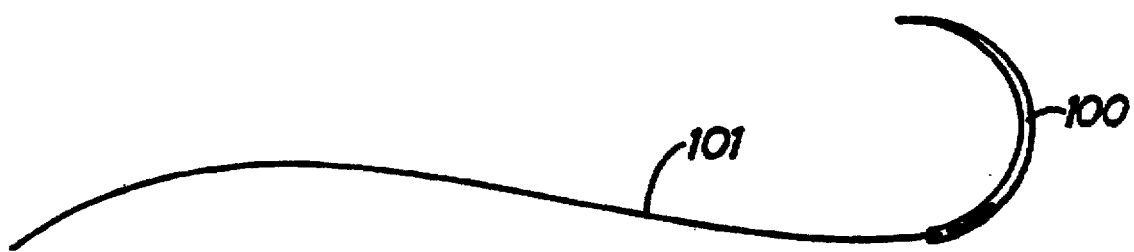
FIG. 1 is a perspective view of a coated suture attached to a needle described herein.

It has been found that fatty acid esters and caprolactone containing polymers can advantageously be mixed to form a composition (with fatty acid esters as the predominant component thereof) useful in coating surgical sutures.

Suitable caprolactone containing copolymers include copolymers which may be synthesized by well known conventional polymerization techniques; see, for example Principles of polymerization. George Odian, III Edition; 1991 pp.569–573, the contents of which are incorporated herein by reference.

Preferably, the caprolactone containing copolymer is obtained by polymerizing a major amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

The copolymer herein can contain from about 70 to about 98, and preferably from about 80 to about 95, weight percent epsilon-caprolactone derived units, the balance of the copolymer being derived from the other copolymerizable monomer(s).

Suitable monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including both alpha hydroxy acids (such as glycolic acid and lactic acid) and beta hydroxyacids (such as beta hydroxybutyric acid and gamma hydroxyvaleric acid); polyalkyl ethers (such as polyethylene glycol and polyloropyline glycol and combinations thereof; with glycolide being a preferred monomer.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in small amounts, e.g., from about 0.01 to about 5, and preferably from about 0.1 to about 3, weight percent of the total monomer mixture.

Suitable esters of fatty acids include esters of the formula:

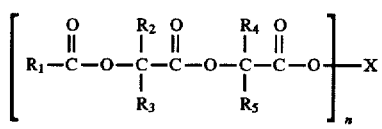

wherein x is an alkaline-earth metal or ion thereof and $R_1$ is $C_{10}$ or greater alkyl, $R_2$ is H, or $C_1$–$C_3$ alkyl, $R_3$ is H, or $C_1$–$C_3$ alkyl, $R_4$ is H, or $C_1$–$C_3$ alkyl, $R_5$ is H, or $C_1$–$C_3$ alkyl, and n>1. Such suitable fatty acids include calcium, magnesium, aluminum, barium, or zinc stearoyl lactylate; calcium, magnesium, aluminum, barium, or zinc palmityl lactylate; calcium, magnesium, aluminum, barium, or zinc olelyl lactylate; with calcium stearoyl-2-lactylate (such as the calcium stearoyl-2-lactylate commercially available under the tradename VERV from American Ingredients Co., Kansas City, Mo.) being preferred.

The caprolactone containing copolymer and the fatty acid ester are non-toxic; a mixture of the two is non-toxic as well.

The bioabsorbable mixture herein can be applied to a suture by any suitable process, e.g. passing the suture through a solution of the copolymer, e.g. in toluene, methylene chloride, etc., past a brush or other coating solution applicator, or past one or more spray nozzles dispensing the suture coating solution. The suture wetted with the coating solution is subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

While the coating composition herein can be applied to any type of suture, it is essentially intended for application to a braided suture, a preferred type of which is disclosed in U.S. Pat. No. 5,019,093. The amount of coating composition applied to a braided suture will vary depending upon the structure of the suture, e.g., the number of filaments, tightness of braid or twist, the size of the suture and its composition. Suitable coating levels range from about 0.3% to about 10% with about 0.5% to about 5% being preferred.

The coated suture, suture 101, may be attached to a surgical needle 100 as shown in FIG. 1 by methods well known in the art. Wounds may be sutured by passing the needled suture through tissue to create wound closure. The needle preferably is then removed from the suture and the suture tied. The coating advantageously enhances the surgeon's ability to pass the suture through tissue as well as to increase the ease and security with which he/she can tie the suture.

The following examples are given as an illustration of the preparation of copolymers, blends and coatings described herein as well as of the preparation and superior characteristics of the sutures described herein. It should be noted that the invention is not limited to the specific details embodied in the examples.

EXAMPLE 1

Dry glycolide (222 g), epsilon-caprolactone (2000 g), stannous octoate as catalyst (0.44 g) and dry mannitol as initiator (2.2 g) were mixed under $N_2$ for one hour. The mixture was heated in a reactor at a temperature of 160° C. for 12 hours. The epsilon-caprolactone/glycolide star copolymer was then sampled.

1820 g of toluene were mixed with 180 grams of the reaction product at 90° C. for 2 hours under constant stirring, to form a solution.

EXAMPLE 2

1820 g of toluene were mixed with 180 grams of calcium stearoyl lactylate (commercially available from American Ingredients Co., Kansas City, Mo., under the tradename VERV) at 90° C. for one hour under constant stirring to form a solution.

EXAMPLE 3

1000 g of the solution of Example 1 were mixed with 1000 grams of the solution of Example 2 at 25° C. for 10 minutes under constant stirring to form the coating solution.

EXAMPLE 4

A size 0 Polysorb surgical suture was drawn through a coating solution applicator which applied the coating solution of Example 3, at a level of about 3.1 percent by weight of the suture, to coat the suture with the coating solution.

After drying the sutures in an oven for 16 hours, performance characteristics of the sutures, e.g., Surgeon's Throw, Knot Reposition and Knot Security, were measured on a standard tie board.

COMPARATIVE EXAMPLE 1

This was a size 0 suture commercially available from Ethicon, Inc. (Sommerville, N.J.) under the name Vicryl.

COMPARATIVE EXAMPLE 2

Trimethylene carbonate (hereinafter TMC) (1200 grams) and glycolide (2800 grams) were added to a reactor along with 0.4 grams of stannous octoate and about 7 grams to about 8 grams of diethylene glycol. The mixture was heated and placed at 160° C., with stirring under a nitrogen atmosphere for 5 hours. The TMC/glycolide copolymer was then sampled.

1820 g of toluene were mixed with 180 grams of the TMC/glycolide copolymer for two hours to form a solution. The solution was then mixed with 2000 g of the solution of Example 2 for 10 minutes hours under constant stirring to form a coating solution.

Then size 0 Polysorb suture was drawn through a coating applicator, which applied the TMC/glycolide containing coating solution at a level of about 1.3 percent by weight of the suture to coat the suture with the coating solution.

After drying the sutures under vacuum for 16 hours, performance characteristics of the sutures, e.g., Surgeon's Throw, Knot Reposition, and Knot Security, were measured on a standard tie board.

A tie board consists of a base on which two plates are perpendicularly affixed. These plates are parallel to one another on the base and are separated by a distance of at least 3 inches. Each plate contains two oppositely disposed openings, the distance between the openings on one plate being longer than that of the other plate. An elastic tube is passed through the openings on both plates to complete a loop which is then tied to secure the loop to the plates. The loop is in the general configuration of an isosceles triangle. To perform the Surgeon's Throw and Knot Reposition tests as described below, a suture is looped and tied around the elastic tube of the tie board and tied. The elastic tube exerts an outward force on the suture knot. This force approximates the force exerted by living tissue on suture knots. Thus, the tie board is an effective means of evaluating the performance characteristics of surgical sutures.

The procedures for evaluating these performance characteristics are described in Table I as follows:

TABLE I

PROCEDURES FOR MEASURING PERFORMANCE
CHARACTERISTICS OF COATED SUTURES

| Performance Characteristic | Test Procedure |
| --- | --- |
| Surgeon's Throw | A suture is looped around the elastic tubes of a tie board and tied with a surgeon's throw (a half hitch with an extra loop of the free end). The ends are pulled apart by hand and the suture loop pulls the elastic tubes of the tie board together. The ends of the suture are then released. If the tubes stay together for approximately ten seconds, the trial is counted as a "pass". If the surgeon's throw slips and the tubes move apart, the trial is counted as a "failure". |
| Knot Reposition | A suture is looped around the elastic tubes of a tie board and tied with two half hitches in the same direction (a granny knot). The free ends of the suture are pulled apart by hand. If the knot slips and the loop of the suture pulls the elastic tubes of the tie board together, the knot is said to reposition and the trial is counted as a "pass". If the suture breaks or if the knot locks in place and cannot be moved, the trial is counted as a "failure". |
| Knot Security | A 2 cm loop is tied with a surgeon's square knot (1 = 1 = 1 = 1) securing the throws at 20% of the USP XXII knot strength for 2/0 nonabsorbable sutures (n = 10 loops per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. For each pass of the cloth across the knot (for a total of 100 passes), the knot is inspected for top throw security. For a knot to be considered secure, there must be no relaxation of the knot or loss of the fourth throw. |

The test results are set forth in Table II below:

TABLE II

PERFORMANCE CHARACTERISTICS OF SUTURES

| Example | Coating Level (%) | Surgeon's Throw (No. of passes/ 10 attempts) | Knot Reposition (No. of passes/ 10 attempts) | Knot Security (No. failures per 10 attempts) |
| --- | --- | --- | --- | --- |
| Example 4 | 3.1 | 9 | 9 | 0 |
| Comparative Example 1 (Vicryl size 0 suture) | 1.8 | 9 | 8 | 0 |
| Comparative Example 2 (size 0 polysorb suture coated with a mixture of VERV and a copolymer of TMC and glycolide | 3.1 | 10 | 4 | 0 |

As the data in Table II illustrates, the suture coated with the mixture of fatty acid ester and caprolactone containing copolymer performs comparable to or better than commercially available Vicryl suture and shows substantially improved knot reposition over Comparative Example 2.

It will be understood that various modifications may be made to the embodiments disclosed herein. For example, although it is preferred to coat surgical sutures from the disclosed mixtures, a wide variety of surgical articles can be coated. These include but are not limited to clips and other fasteners, staples, pins, screws, prosthetic devices, drug delivery devices, meshes or fabrics, anastomosis rings, and other implantable devices. Therefore, the above description should not be construed as limiting, but merely as exemplifications of preferred embodiments. Those skilled in the art will envision other modifications within the scope and spirit of the claims appended hereto.

What is claimed is:

1. A surgical suture coating comprising:
   a) a copolymer comprising a predominant amount of epsilon-caprolactone and a minor amount of at least one other copolymerizable monomer: and
   b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, and zinc olelyl lactylate.

2. The surgical suture of claim 1 wherein the coating comprises from about 5 to about 95 percent by weight of the copolymer component; the remainder being the salt of a lactylate ester of a $C_{10}$ or greater fatty acid.

3. A surgical suture coating comprising:
   a) copolymer comprising a predominant amount of epsilon-caprolactone and a minor amount of at least one other copolymerizable monomer; and
   b) calcium stearoyl lactylate.

4. The surgical suture of claim 3, wherein the suture is a braided suture.

5. The surgical suture of claim 3 wherein the coating comprises from about 5 to about 95 percent by weight of the copolymer component; the remainder being calcium stearoyl lactylate.

6. The surgical suture of claim 3 wherein the copolymer component comprises a reaction product obtained by polymerizing a major amount of epsilon-caprolactone and a minor amount of at least one other copolymerizable monomer in the presence of polyhydric alcohol as initiator.

7. The surgical suture of claim 6, wherein the other copolymerizable monomer is selected from the group consisting of alkylene carbonates, dioxanones, dioxepanones, absorbable cyclic amides, absorbable cyclic ether-esters derived from crown ethers, hydroxyacids capable of esterification, and combinations thereof.

8. The surgical suture of claim 7, wherein the other copolymerizable monomer is selected from the group consisting of glycolide, lactide, p-dioxanone and trimethylene carbonate.

9. The surgical suture of claim 7, containing from about 80 to about 95 weight percent epsilon-caprolactone-derived units, the balance of the copolymer being derived from at least one other copolymerizable monomer.

10. The surgical suture of claim 9, wherein the other copolymerizable monomer is glycolide.

11. The surgical suture of claim 6, wherein the polyhydric alcohol initiator is selected from the group consisting of glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxy-ethyl)ethylenediamine, N,N, N',N'-tetrakis(2-hydroxypropyl) ethylenediamine, dipentaerythritol, allitol, dulcitol, glucitol, altritol, iditol, sorbitol, mannitol and inositol.

12. The surgical suture of claim 11, wherein the polyhydric alcohol is employed in an amount of from about 0.5 to about 5 weight percent of the total monomer mixture.

13. A suture coated with a composition fabricated from a blend of a up to about 50 weight percent of a copolymer the remainder being a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, zinc olelyl lactylate and calcium stearoyl lactylate, said copolymer comprising the reaction product obtained by polymerizing a major amount of epsilon-caprolactone and a minor amount of at least one other copolymerizable monomer in the presence of polyhydric alcohol as initiator.

14. The suture of claim 13, is exhibiting the following properties:

at most knot run down about 1/10 failures;

at most knot security about 0/10 failures;

at most surgeon's throw about 1/10 failures.

15. A method of suturing a wound comprising:

a) providing a needled suture, said suture being coated with a composition comprising a mixture of
   1) a copolymer comprising the reaction product obtained by polymerizing a major amount of epsilon-caprolactone and a minor amount of at least one other copolymerizable monomer in the presence of polyhydric alcohol as initiator; and
   2) a lactylate ester of a $C_{10}$ or greater fatty acid selected from the group consisting of magnesium stearoyl lactylate, aluminum stearoyl lactylate, barium stearoyl lactylate zinc stearoyl lactylate, calcium palmityl lactylate, magnesium palmityl lactylate, aluminum palmityl lactylate barium palmityl lactylate, or zinc palmityl lactylate, calcium olelyl lactylate, magnesium olelyl lactylate, aluminum olelyl lactylate, barium olelyl lactylate, zinc olelyl lactylate and calcium stearoyl lactylate; and b) passing said needled suture through tissue to create wound closure.

16. An implantable medical device having a coating comprising a mixture of a) a copolymer comprising a predominant amount of epsilon-caprolactone and a minor amount of at least one other copolymerizable monomer; and b) the salt of a lactylate ester of a $C_{10}$ or greater fatty acid selected from the group consisting of magnesium stearoyl lactylate, aluminum stearoyl lactylate, barium stearoyl lactylate, zinc stearoyl lactylate calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, zinc olelyl lactylate and calcium stearoyl lactylate.

17. The implantable medical device of claim 16 wherein said medical device is selected from the group consisting of clips, staples, pins, screws, prosthetic devices, anastomosis rings, and growth matrices.

* * * * *